(12) United States Patent
Miller (10) Patent No.: US 7,699,850 B2
(45) Date of Patent: Apr. 20, 2010

(54) APPARATUS AND METHOD TO ACCESS BONE MARROW

(75) Inventor: Larry J. Miller, Spring Branch, TX (US)

(73) Assignee: Vidacare Corporation, San Antonio, TX (US)

( * ) Notice: Subject to any disclaimer, the term of this patent is extended or adjusted under 35 U.S.C. 154(b) by 509 days.

(21) Appl. No.: 10/449,476

(22) Filed: May 30, 2003

(65) Prior Publication Data

US 2003/0225411 A1 Dec. 4, 2003

Related U.S. Application Data

(60) Provisional application No. 60/384,756, filed on May 31, 2002.

(51) Int. Cl.
*A61B 17/16* (2006.01)
(52) U.S. Cl. ........................................................ 606/80
(58) Field of Classification Search .................. 606/80, 606/180, 79, 185; 600/562, 564–567
See application file for complete search history.

(56) References Cited

U.S. PATENT DOCUMENTS

| | | | |
|---|---|---|---|
| 1,539,637 A | 5/1925 | Bronner | |
| 2,317,648 A | 4/1943 | Siqveland | 32/26 |
| 2,419,045 A | 4/1947 | Whittaker | 128/305 |
| 2,773,501 A | 12/1956 | Young | 128/221 |
| 3,104,448 A | 9/1963 | Morrow et al. | |
| 3,120,845 A | 2/1964 | Horner | 128/310 |
| 3,173,417 A | 3/1965 | Horner | 128/305 |
| 3,175,554 A | 3/1965 | Stewart | 128/2 |
| 3,507,276 A | 4/1970 | Burgess et al. | 128/173 |
| 3,543,966 A | 12/1970 | Ryan et al. | 222/94 |
| 3,815,605 A | 6/1974 | Schmidt et al. | 128/305 |
| 3,835,860 A | 9/1974 | Garretson | |
| 3,893,445 A | 7/1975 | Hofsess | 128/2 |
| 3,893,455 A | 7/1975 | Hofsess | 128/2 B |
| 3,991,765 A | 11/1976 | Cohen | 128/305 |

(Continued)

FOREIGN PATENT DOCUMENTS

CA 2 454 600 1/2004

(Continued)

OTHER PUBLICATIONS

Communication relating to the results of the partial International Search Report for PCT/US2005/002484, 6 pages, mailed May 19, 2005.

(Continued)

*Primary Examiner*—Thomas C Barrett
*Assistant Examiner*—Michael J. Araj
(74) *Attorney, Agent, or Firm*—Baker Botts L.L.P.

(57) ABSTRACT

An apparatus and method for penetrating bone marrow is provided. The apparatus may include a housing such as a handheld body, a penetrator assembly, a connector that releasably attaches the penetrator assembly to a drill shaft, a gear mechanism, a motor and a power supply and associated circuitry operable to power the motor. The penetrator assembly may include a removable inner trocar and an outer penetrator or needle. It may also include a grooved trocar that allows bone chips to be expelled as the apparatus is inserted into bone marrow. Various connectors are provided to attach the penetrator assembly to the drill shaft.

13 Claims, 10 Drawing Sheets

U.S. PATENT DOCUMENTS

| | | | |
|---|---|---|---|
| 4,021,920 A | 5/1977 | Kirschner et al. | |
| 4,099,518 A | 7/1978 | Baylis et al. | 600/567 |
| 4,124,026 A | 11/1978 | Berner et al. | 606/104 |
| 4,142,517 A | 3/1979 | Stavropoulos et al. | 128/2 B |
| 4,170,993 A | 10/1979 | Alvarez | 128/214 |
| 4,185,619 A | 1/1980 | Reiss | |
| 4,194,505 A | 3/1980 | Schmitz | 128/218 |
| 4,258,722 A | 3/1981 | Sessions et al. | 128/753 |
| 4,262,676 A | 4/1981 | Jamshidi | 128/753 |
| 4,306,570 A | 12/1981 | Matthews | 128/754 |
| 4,333,459 A | 6/1982 | Becker | |
| 4,381,777 A | 5/1983 | Garnier | 604/188 |
| 4,441,563 A | 4/1984 | Walton, II | |
| 4,469,109 A | 9/1984 | Mehl | 128/753 |
| 4,484,577 A | 11/1984 | Sackner et al. | 128/203.28 |
| 4,543,966 A | 10/1985 | Islam et al. | 128/754 |
| 4,553,539 A | 11/1985 | Morris | 128/132 D |
| 4,605,011 A | 8/1986 | Naslund | 128/752 |
| 4,620,539 A | 11/1986 | Andrews et al. | |
| 4,646,731 A | 3/1987 | Brower | 128/156 |
| 4,654,492 A | 3/1987 | Koerner et al. | 200/153 |
| 4,655,226 A | 4/1987 | Lee | 128/754 |
| 4,659,329 A | 4/1987 | Annis | 604/180 |
| 4,692,073 A * | 9/1987 | Martindell | 408/239 A |
| 4,711,636 A | 12/1987 | Bierman | 604/180 |
| 4,713,061 A | 12/1987 | Tarello et al. | |
| 4,716,901 A | 1/1988 | Jackson et al. | |
| 4,723,945 A | 2/1988 | Theiling | 604/232 |
| 4,758,225 A | 7/1988 | Cox et al. | 604/126 |
| 4,762,118 A | 8/1988 | Lia et al. | 128/4 |
| 4,772,261 A | 9/1988 | Von Hoff et al. | 604/51 |
| 4,787,893 A | 11/1988 | Villette | 604/188 |
| 4,793,363 A * | 12/1988 | Ausherman et al. | 600/567 |
| 4,867,158 A | 9/1989 | Sugg | 128/305.1 |
| 4,919,146 A | 4/1990 | Rhinehart et al. | 128/752 |
| 4,921,013 A | 5/1990 | Spalink et al. | 137/614.05 |
| 4,935,010 A | 6/1990 | Cox et al. | 604/122 |
| 4,940,459 A | 7/1990 | Noce | 604/98 |
| 4,944,677 A | 7/1990 | Alexandre | 433/165 |
| 4,969,870 A * | 11/1990 | Kramer et al. | 604/506 |
| 4,986,279 A | 1/1991 | O'Neill | 128/754 |
| 5,002,546 A | 3/1991 | Romano | 606/80 |
| 5,025,797 A | 6/1991 | Baran | 128/754 |
| 5,036,860 A | 8/1991 | Leigh et al. | 128/754 |
| 5,057,085 A | 10/1991 | Kopans | 604/173 |
| 5,074,311 A | 12/1991 | Hasson | 128/754 |
| 5,116,324 A | 5/1992 | Brierley et al. | 604/180 |
| 5,120,312 A | 6/1992 | Wigness et al. | 604/175 |
| 5,122,114 A | 6/1992 | Miller et al. | 604/49 |
| 5,133,359 A | 7/1992 | Kedem | 128/754 |
| 5,137,518 A | 8/1992 | Mersch | 604/168 |
| 5,139,500 A | 8/1992 | Schwartz | 606/96 |
| RE34,056 E | 9/1992 | Lindgren et al. | 128/754 |
| 5,172,701 A | 12/1992 | Leigh | 128/753 |
| 5,172,702 A | 12/1992 | Leigh et al. | 128/754 |
| 5,176,643 A | 1/1993 | Kramer et al. | 604/135 |
| 5,195,985 A | 3/1993 | Hall | 604/195 |
| 5,203,056 A | 4/1993 | Funk et al. | 24/543 |
| 5,207,697 A | 5/1993 | Carusillo et al. | 606/167 |
| 5,249,583 A | 10/1993 | Mallaby | 128/754 |
| 5,257,632 A | 11/1993 | Turkel et al. | 128/754 |
| 5,269,785 A | 12/1993 | Bonutti | 606/80 |
| 5,279,306 A | 1/1994 | Mehl | 128/753 |
| 5,312,364 A | 5/1994 | Jacobs | 604/180 |
| 5,324,300 A | 6/1994 | Elias et al. | 606/180 |
| 5,332,398 A | 7/1994 | Miller et al. | 604/175 |
| 5,333,790 A | 8/1994 | Christopher | 239/391 |
| 5,341,823 A | 8/1994 | Manosalva et al. | 128/898 |
| 5,348,022 A | 9/1994 | Leigh et al. | 128/753 |
| 5,357,974 A | 10/1994 | Baldridge | 128/754 |
| 5,368,046 A | 11/1994 | Scarfone et al. | 128/754 |
| 5,372,583 A | 12/1994 | Roberts et al. | 604/51 |
| 5,383,859 A | 1/1995 | Sewell, Jr. | 604/164 |
| 5,385,553 A | 1/1995 | Hart et al. | |
| 5,400,798 A | 3/1995 | Baran | 128/754 |
| 5,405,348 A | 4/1995 | Anspach et al. | 606/80 |
| 5,423,824 A | 6/1995 | Akerfeldt et al. | 606/80 |
| 5,431,655 A | 7/1995 | Melker et al. | 606/79 |
| 5,451,210 A | 9/1995 | Kramer et al. | 604/137 |
| 5,484,442 A | 1/1996 | Melker et al. | 606/79 |
| D369,858 S | 5/1996 | Baker et al. | D24/112 |
| 3,529,580 A | 6/1996 | Kusunoki et al. | |
| 5,526,821 A | 6/1996 | Jamshidi | 128/753 |
| 5,529,580 A | 6/1996 | Kusunoki et al. | |
| 5,549,565 A | 8/1996 | Ryan et al. | 604/167 |
| 5,554,154 A | 9/1996 | Rosenberg | 606/80 |
| 5,556,399 A | 9/1996 | Huebner | 606/80 |
| 5,558,737 A | 9/1996 | Brown et al. | 156/172 |
| 5,571,133 A | 11/1996 | Yoon | 606/185 |
| 5,586,847 A * | 12/1996 | Mattern et al. | 408/239 A |
| 5,591,188 A | 1/1997 | Waisman | 606/182 |
| 5,595,186 A | 1/1997 | Rubinstein et al. | 600/567 |
| 5,601,559 A | 2/1997 | Melker et al. | 606/79 |
| 5,632,747 A | 5/1997 | Scarborough et al. | 606/79 |
| 5,713,368 A | 2/1998 | Leigh | 128/753 |
| 5,724,873 A * | 3/1998 | Hillinger | 81/451 |
| 5,733,262 A | 3/1998 | Paul | 604/116 |
| 5,752,923 A | 5/1998 | Terwilliger | 600/562 |
| 5,762,639 A | 6/1998 | Gibbs | 604/272 |
| 5,766,221 A | 6/1998 | Benderev et al. | 606/232 |
| 5,769,086 A | 6/1998 | Ritchart et al. | 128/753 |
| 5,779,708 A | 7/1998 | Wu | 606/80 |
| 5,800,389 A | 9/1998 | Burney et al. | 604/93 |
| 5,807,277 A | 9/1998 | Swaim | 600/567 |
| 5,810,826 A | 9/1998 | Akerfeldt et al. | 606/80 |
| 5,817,052 A | 10/1998 | Johnson et al. | 604/51 |
| 5,823,970 A | 10/1998 | Terwilliger | 600/564 |
| D403,405 S | 12/1998 | Terwilliger | D24/130 |
| 5,858,005 A | 1/1999 | Kriesel | 604/180 |
| 5,865,711 A | 2/1999 | Kramer et al. | 604/136 |
| 5,868,711 A | 2/1999 | Kramer et al. | 604/136 |
| 5,868,750 A | 2/1999 | Schultz | 606/104 |
| 5,873,510 A | 2/1999 | Hirai et al. | |
| 5,885,226 A | 3/1999 | Rubinstein et al. | |
| 5,891,085 A | 4/1999 | Lilley et al. | 604/68 |
| 5,911,701 A | 6/1999 | Miller et al. | 604/22 |
| 5,911,708 A | 6/1999 | Teirstein | 604/183 |
| 5,916,229 A | 6/1999 | Evans | 606/171 |
| 5,919,172 A | 7/1999 | Golba, Jr. | 604/272 |
| 5,924,864 A * | 7/1999 | Loge et al. | 433/118 |
| 5,927,976 A | 7/1999 | Wu | 433/82 |
| 5,928,238 A | 7/1999 | Scarborough et al. | 606/79 |
| 5,941,706 A | 8/1999 | Ura | 433/165 |
| 5,941,851 A | 8/1999 | Coffey et al. | |
| 5,960,797 A * | 10/1999 | Kramer et al. | 128/899 |
| 5,980,545 A | 11/1999 | Pacala et al. | 606/170 |
| 5,993,417 A | 11/1999 | Yerfino et al. | |
| 5,993,454 A | 11/1999 | Longo | 606/80 |
| 6,007,496 A | 12/1999 | Brannon | 600/565 |
| 6,017,348 A | 1/2000 | Hart et al. | 606/79 |
| 6,018,094 A | 1/2000 | Fox | 623/11 |
| 6,022,324 A | 2/2000 | Skinner | 600/566 |
| 6,027,458 A | 2/2000 | Janssens | 600/567 |
| 6,033,369 A | 3/2000 | Goldenberg | 600/567 |
| 6,033,411 A | 3/2000 | Preissman | 606/99 |
| 6,063,037 A | 5/2000 | Mittermeier et al. | |
| 6,071,284 A | 6/2000 | Fox | 606/80 |
| 6,080,115 A | 6/2000 | Rubinstein | |
| 6,083,176 A | 7/2000 | Terwilliger | 600/562 |
| 6,086,543 A | 7/2000 | Anderson et al. | 600/567 |
| 6,086,544 A | 7/2000 | Hibner et al. | 600/568 |
| 6,096,042 A | 8/2000 | Herbert | 606/80 |
| 6,102,915 A | 8/2000 | Bresler et al. | |
| 6,106,484 A | 8/2000 | Terwilliger | 600/568 |

| Patent No. | Date | Inventor | Class |
|---|---|---|---|
| 6,110,128 A | 8/2000 | Andelin et al. | |
| 6,110,129 A | 8/2000 | Terwilliger | 600/567 |
| 6,110,174 A | 8/2000 | Nichter | 606/72 |
| 6,120,462 A | 9/2000 | Hibner et al. | 600/566 |
| 6,135,769 A | 10/2000 | Kwan | 433/80 |
| 6,159,163 A | 12/2000 | Strauss et al. | 600/566 |
| 6,162,203 A | 12/2000 | Haaga | |
| 6,183,442 B1 | 2/2001 | Athanasiou et al. | 604/154 |
| 6,210,376 B1 | 4/2001 | Grayson | 604/264 |
| 6,217,561 B1 | 4/2001 | Gibbs | 604/264 |
| 6,221,029 B1 | 4/2001 | Mathis et al. | 600/564 |
| 6,228,049 B1 | 5/2001 | Schroeder et al. | 604/93.01 |
| 6,228,088 B1 | 5/2001 | Miller et al. | 606/80 |
| 6,238,355 B1 | 5/2001 | Daum | 600/567 |
| 6,247,928 B1 | 6/2001 | Meller et al. | 433/80 |
| 6,248,110 B1 | 6/2001 | Reiley et al. | 606/93 |
| 6,257,351 B1 | 7/2001 | Ark et al. | |
| 6,273,715 B1 | 8/2001 | Meller et al. | 433/80 |
| 6,273,862 B1 | 8/2001 | Privitera et al. | 600/568 |
| 6,283,925 B1 | 9/2001 | Terwilligr | 600/568 |
| 6,283,970 B1 | 9/2001 | Lubinus | 606/80 |
| 6,287,114 B1 | 9/2001 | Meller et al. | 433/80 |
| 6,302,852 B1 | 10/2001 | Fleming, III et al. | 600/567 |
| 6,309,358 B1 | 10/2001 | Okubo | 600/466 |
| 5,315,737 A1 | 11/2001 | Skinner | 600/566 |
| 6,312,394 B1 | 11/2001 | Fleming, III | 600/567 |
| 6,315,737 B1 | 11/2001 | Skinner | 600/566 |
| 6,325,806 B1 | 12/2001 | Fox | 606/80 |
| 6,328,701 B1 | 12/2001 | Terwilliger | 600/567 |
| 6,328,744 B1 | 12/2001 | Harari et al. | 606/80 |
| 6,358,252 B1 | 3/2002 | Shapira | 606/80 |
| 6,402,701 B1 | 6/2002 | Kaplan et al. | 600/567 |
| 6,419,490 B1 | 7/2002 | Kitchings Weathers, Jr. | 433/165 |
| 6,425,888 B1 | 7/2002 | Embleton et al. | 604/290 |
| 6,428,487 B1 | 8/2002 | Burdorff et al. | 600/568 |
| 6,443,910 B1 | 9/2002 | Krueger et al. | 600/567 |
| 6,468,248 B1 | 10/2002 | Gibbs | 604/164.01 |
| 6,478,751 B1 | 11/2002 | Krueger et al. | 600/566 |
| 6,488,636 B2 | 12/2002 | Bryan et al. | 600/565 |
| 6,523,698 B1 | 2/2003 | Dennehey et al. | 210/435 |
| 6,527,736 B1 | 3/2003 | Attinger et al. | 604/43 |
| 6,527,778 B2 | 3/2003 | Athanasiou et al. | |
| 6,540,694 B1 | 4/2003 | Van Bladel et al. | 600/564 |
| 6,547,511 B1 | 4/2003 | Adams | |
| 6,547,561 B2 | 4/2003 | Meller et al. | 433/80 |
| 6,554,779 B2 | 4/2003 | Viola et al. | 600/568 |
| 6,555,212 B2 | 4/2003 | Boiocchi et al. | 428/295.4 |
| 6,582,399 B1 | 6/2003 | Smith et al. | 604/152 |
| 6,585,622 B1 | 7/2003 | Shum et al. | 482/8 |
| 6,595,911 B2 | 7/2003 | LoVuolo | 600/30 |
| 6,595,979 B1 | 7/2003 | Epstein et al. | 604/506 |
| 6,613,054 B2 | 9/2003 | Scribner et al. | 606/93 |
| 6,616,632 B2 | 9/2003 | Sharp et al. | 604/117 |
| 6,620,111 B2 | 9/2003 | Stephens et al. | 600/567 |
| 6,626,848 B2 | 9/2003 | Neuenfeldt | |
| 6,626,887 B1 | 9/2003 | Wu | 604/512 |
| 6,638,235 B2 | 10/2003 | Miller et al. | 600/566 |
| 6,656,133 B2 | 12/2003 | Voegele et al. | |
| 6,689,072 B2 | 2/2004 | Kaplan et al. | 600/567 |
| 6,702,760 B2 | 3/2004 | Krause et al. | 600/564 |
| 6,702,761 B1 | 3/2004 | Damadian et al. | 600/576 |
| 6,706,016 B2 | 3/2004 | Cory et al. | 604/117 |
| 6,716,192 B1 | 4/2004 | Orosz, Jr. | 604/117 |
| 6,716,215 B1 | 4/2004 | David et al. | 606/80 |
| 6,716,216 B1 | 4/2004 | Boucher et al. | 606/86 |
| 6,730,043 B2 | 5/2004 | Krueger et al. | |
| 6,730,044 B2 | 5/2004 | Stephens et al. | 600/568 |
| 6,749,576 B2 | 6/2004 | Bauer | 600/567 |
| 6,752,768 B2 | 6/2004 | Burdorff et al. | 600/568 |
| 6,752,816 B2 | 6/2004 | Culp et al. | 606/170 |
| 6,758,824 B1 | 7/2004 | Miller et al. | 600/568 |
| 6,761,726 B1 | 7/2004 | Findlay et al. | 606/182 |
| 6,796,957 B2 | 9/2004 | Carpenter et al. | 604/93.01 |
| 6,846,314 B2 | 1/2005 | Shapira | 606/80 |
| 6,849,051 B2 | 2/2005 | Sramek et al. | 600/565 |
| 6,855,148 B2 | 2/2005 | Foley et al. | 606/86 |
| 6,860,860 B2 | 3/2005 | Viola | 600/564 |
| 6,875,183 B2 | 4/2005 | Cervi | |
| 6,875,219 B2 | 4/2005 | Arramon et al. | 606/92 |
| 6,884,245 B2 | 4/2005 | Spranza, III | 606/79 |
| 6,887,209 B2 | 5/2005 | Kadziauskas et al. | 600/565 |
| 6,890,308 B2 | 5/2005 | Islam | |
| 6,905,486 B2 | 6/2005 | Gibbs | 604/264 |
| 6,930,461 B2 | 8/2005 | Rutkowski | |
| 6,942,669 B2 | 9/2005 | Kurc | 606/80 |
| 6,969,373 B2 | 11/2005 | Schwartz et al. | 604/170.03 |
| 7,008,381 B2 | 3/2006 | Janssens | 600/564 |
| 7,008,383 B1 | 3/2006 | Damadian et al. | 600/567 |
| 7,008,394 B2 | 3/2006 | Geise et al. | 615/6.15 |
| 7,025,732 B2 | 4/2006 | Thompson et al. | 600/654 |
| 7,063,672 B2 | 6/2006 | Schramm | |
| 7,137,985 B2 | 11/2006 | Jahng | 606/61 |
| 7,207,949 B2 | 4/2007 | Miles et al. | 600/554 |
| 7,226,450 B2 | 6/2007 | Athanasiou et al. | 606/80 |
| 7,229,401 B2 | 6/2007 | Kindlein | 600/7 |
| 2001/0005778 A1 | 6/2001 | Ouchi | 600/564 |
| 2001/0014439 A1* | 8/2001 | Meller et al. | 433/50 |
| 2001/0047183 A1 | 11/2001 | Privitera et al. | 606/170 |
| 2001/0053888 A1 | 12/2001 | Athanasiou et al. | |
| 2002/0042581 A1 | 4/2002 | Cervi | |
| 2002/0055713 A1 | 5/2002 | Gibbs | |
| 2002/0120212 A1 | 8/2002 | Ritchart et al. | 600/567 |
| 2002/0138021 A1 | 9/2002 | Pflueger | |
| 2002/0143269 A1 | 10/2002 | Neuenfeldt | |
| 2002/0151821 A1 | 10/2002 | Castellacci | |
| 2003/0028146 A1 | 2/2003 | Aves | 604/164.06 |
| 2003/0032939 A1 | 2/2003 | Gibbs | 604/510 |
| 2003/0036747 A1 | 2/2003 | Ie et al. | 606/1 |
| 2003/0050574 A1 | 3/2003 | Krueger | 600/567 |
| 2003/0114858 A1 | 6/2003 | Athanasiou et al. | 606/80 |
| 2003/0125639 A1 | 7/2003 | Fisher et al. | 600/564 |
| 2003/0153842 A1 | 8/2003 | Lamoureux et al. | 600/564 |
| 2003/0191414 A1 | 10/2003 | Reiley et al. | 600/567 |
| 2003/0195436 A1 | 10/2003 | Van Bladel et al. | 600/584 |
| 2003/0199787 A1 | 10/2003 | Schwindt | 600/568 |
| 2003/0216667 A1 | 11/2003 | Viola | 600/564 |
| 2003/0225344 A1 | 12/2003 | Miller | 600/568 |
| 2003/0225364 A1 | 12/2003 | Kraft et al. | 604/35 |
| 2003/0225411 A1 | 12/2003 | Miller | 606/80 |
| 2004/0019297 A1 | 1/2004 | Angel | 600/564 |
| 2004/0019299 A1 | 1/2004 | Ritchart et al. | 600/567 |
| 2004/0034280 A1 | 2/2004 | Privitera et al. | 600/170 |
| 2004/0049128 A1 | 3/2004 | Miller et al. | 600/566 |
| 2004/0064136 A1 | 4/2004 | Papineau et al. | 606/41 |
| 2004/0073139 A1 | 4/2004 | Hirsch et al. | 600/564 |
| 2004/0092946 A1 | 5/2004 | Bagga et al. | 606/93 |
| 2004/0153003 A1 | 8/2004 | Cicenas et al. | 600/564 |
| 2004/0158172 A1 | 8/2004 | Hancock | 600/564 |
| 2004/0158173 A1 | 8/2004 | Voegele et al. | 600/568 |
| 2004/0162505 A1 | 8/2004 | Kaplan et al. | 600/567 |
| 2004/0191897 A1 | 9/2004 | Muschler | 435/325 |
| 2004/0210161 A1 | 10/2004 | Burdorff et al. | 600/566 |
| 2004/0215102 A1 | 10/2004 | Ikehara et al. | 600/562 |
| 2004/0220497 A1 | 11/2004 | Findlay et al. | 600/562 |
| 2005/0027210 A1 | 2/2005 | Miller | 600/567 |
| 2005/0040060 A1 | 2/2005 | Andersen et al. | 206/363 |
| 2005/0075581 A1 | 4/2005 | Schwindt | 600/568 |
| 2005/0085838 A1 | 4/2005 | Thompson et al. | 606/170 |
| 2005/0101880 A1 | 5/2005 | Cicenas et al. | 600/567 |
| 2005/0113716 A1 | 5/2005 | Mueller et al. | 600/568 |
| 2005/0124915 A1 | 6/2005 | Eggers et al. | 600/568 |
| 2005/0131345 A1 | 6/2005 | Miller | 604/117 |
| 2005/0148940 A1 | 7/2005 | Miller | 604/187 |
| 2005/0165328 A1 | 7/2005 | Heske et al. | 600/566 |
| 2005/0165403 A1 | 7/2005 | Miller | 606/79 |

| | | | |
|---|---|---|---|
| 2005/0165404 A1 | 7/2005 | Miller | 606/80 |
| 2005/0171504 A1 | 8/2005 | Miller | 604/506 |
| 2005/0182394 A1 | 8/2005 | Spero et al. | 606/21 |
| 2005/0200087 A1 | 9/2005 | Vasudeva et al. | 279/143 |
| 2005/0203439 A1 | 9/2005 | Heske et al. | 600/566 |
| 2005/0209530 A1 | 9/2005 | Pflueger | 600/567 |
| 2005/0215921 A1 | 9/2005 | Hibner et al. | 600/566 |
| 2005/0228309 A1 | 10/2005 | Fisher et al. | 600/562 |
| 2005/0261693 A1 | 11/2005 | Miller et al. | 606/80 |
| 2006/0011506 A1 | 1/2006 | Riley | 206/570 |
| 2006/0015066 A1 | 1/2006 | Turieo et al. | 604/136 |
| 2006/0036212 A1 | 2/2006 | Miller | 604/48 |
| 2006/0052790 A1 | 3/2006 | Miller | 606/80 |
| 2006/0074345 A1 | 4/2006 | Hibner | 600/566 |
| 2006/0079774 A1 | 4/2006 | Anderson | 600/442 |
| 2006/0089565 A1 | 4/2006 | Schramm | 600/568 |
| 2006/0122535 A1 | 6/2006 | Daum | 600/565 |
| 2006/0129082 A1 | 6/2006 | Rozga | 604/6.04 |
| 2006/0144548 A1 | 7/2006 | Beckman et al. | 163/1 |
| 2006/0149163 A1 | 7/2006 | Hibner et al. | 600/566 |
| 2006/0167377 A1 | 7/2006 | Ritchart et al. | 600/566 |
| 2006/0167378 A1 | 7/2006 | Miller | 600/566 |
| 2006/0167379 A1 | 7/2006 | Miller | 600/566 |
| 2006/0184063 A1 | 8/2006 | Miller | 600/568 |
| 2006/0189940 A1 | 8/2006 | Kirsch | 604/164.1 |
| 2007/0016100 A1 | 1/2007 | Miller | 600/567 |
| 2007/0049945 A1 | 3/2007 | Miller | 606/86 |
| 2007/0149920 A1 | 6/2007 | Michels et al. | 604/93.01 |
| 2007/0213735 A1 | 9/2007 | Sandat et al. | 606/79 |
| 2007/0270775 A1 | 11/2007 | Miller et al. | 604/506 |
| 2008/0015467 A1 | 1/2008 | Miller | 600/568 |
| 2008/0015468 A1 | 1/2008 | Miller | 600/568 |
| 2008/0045857 A1 | 2/2008 | Miller et al. | 600/566 |
| 2008/0045860 A1 | 2/2008 | Miller et al. | 600/567 |
| 2008/0045861 A1 | 2/2008 | Miller et al. | 600/567 |
| 2008/0045965 A1 | 2/2008 | Miller et al. | 606/80 |
| 2008/0140014 A1 | 6/2008 | Miller et al. | 604/180 |
| 2008/0215056 A1 | 9/2008 | Miller et al. | 606/80 |
| 2008/0221580 A1 | 9/2008 | Miller et al. | 606/80 |

FOREIGN PATENT DOCUMENTS

| | | |
|---|---|---|
| DE | 10057931 A1 | 11/2000 |
| EP | 517000 | 12/1992 |
| EP | 0807412 A1 | 11/1997 |
| EP | 1314452 | 5/2003 |
| FR | 853349 | 3/1940 |
| FR | 2457105 | 5/1979 |
| FR | 2516386 | 11/1981 |
| GB | 2130890 | 6/1984 |
| JP | 1052433 | 2/1989 |
| WO | 93/07819 | 4/1993 |
| WO | 96/31164 | 10/1996 |
| WO | 98/06337 | 2/1998 |
| WO | 99/18866 | 4/1999 |
| WO | 99/52444 | 10/1999 |
| WO | 00/56220 | 9/2000 |
| WO | 2001/78590 | 10/2001 |
| WO | 02/41791 A1 | 5/2002 |
| WO | 2417921 | 5/2002 |
| WO | 2096497 | 12/2002 |
| WO | 2005110259 | 11/2005 |
| WO | 2005/112800 | 12/2005 |
| WO | 2005112800 | 12/2005 |
| WO | 2008081438 | 7/2008 |

OTHER PUBLICATIONS

International PCT Search Report and Written Opinion PCT/US2004/037753, 16 pages, mailed Jul. 8, 2005.
International PCT Search Report and Written Opinion PCT/US2005/002484, 15 pages, mailed Jul. 22, 2005.
International PCT Search Report PCT/US2004/037753, 6 pages, mailed Apr. 9, 2005.
Riley et al., "A Pathologist's Perspective on Bone Marrow Aspiration Biopsy: I. Performing a Bone Marrow Examination," Journal of Clinical Laboratory Analysis 18, pp. 70-90, 2004.
Richard O. Cummins et al., "ACLS-Principles and Practice", ACLS-The Reference Textbook, American Heart Association, pp. 214-218, 2003.
International PCT Search Report, PCT/US03/17167, 8 pages, mailed Sep. 16, 2003.
International PCT Search Report, PCT/US03/17203, 8 pages, mailed Sep. 16, 2003.
Official Action for European Application No. 03756317.8 (4 pages).
Pediatrics, Official Journal of the American Academy of Pediatrics, Pediatrics, 2005 American Heart Association Guidelines for Cardiopulmonary Resuscitation and Emergency Cardiovascular Care of Pediatric and Neonatal Patients:Pediatric Advanced Life Support, Downloaded from www.pediatrics.org.
International Preliminary Report on Patentability PCT/US2005/002484, 9 pages.
European Office Action EP03731475.4, 4 pages.
Australian Examination Report AU20033240970, 2 pages.
Liakat A. Parapia, Trepanning or trephines: a history of bone marrow biopsy, British Journal of Haematology, pp. 14-19.
U.S. Appl. No. 11/427,501 Non Final Office Action, 14 pages.
International Preliminary Report on Patentability, PCT/US2007/072217, 11 pages.
Aström, K.G., "Automatic Biopsy Instruments Used Through a Coaxial Bone Biopsy System with an Eccentric Drill Tip," Acta Radiologica, 1995; 36:237-242.
Aström, K. Gunnar O., "CT-guided Transsternal Core Biopsy of Anterior Mediastinal Masses," Radiology 1996; 199:564-567.
Pediatric Emergency, Intraosseous Infusion for Administration of Fluids and Drugs, www.cookgroup.com, 1 pg.
Michael Trotty, "Technology (A Special Report) - The Wall Street Journal 2008 Technology Innovation Awards — This years winners include: an IV alternative, a better way to make solar panels, a cheap, fuel efficient car and a better way to see in the dark", The Wall Street Journal, Factiva, 5 pages.
Buckley et al., CT-guided bone biopsy: Initial experience with commercially available hand held Black and Decker drill, European Journal of Radiology 61, pp. 176-180.
Hakan et al., CT-guided Bone BiopsyPerformed by Means of Coaxial Bopsy System with an Eccentric Drill, Radiology, pp. 549-552
European Search Report 08158699.2-1265, 4 pages.
International Search Report and Written Opinion, PCT/US2007/078204, 14 pages.
International Search Report and Written Opinion, PCT/US08/52943, 8 pages.
European Office Action Communication, Application No. 08158699.2-1265/1967142, 10 pages.
Gunal et al., Compartment Syndrome After Intraosseous Infusion: an Expiremental Study in Dogs, Journal of Pediatric Surgery, vol. 31, No. 11, pp. 1491-1493.
International Search Report, PCT/US2007/072217, 20 pages.
International Search Report, PCT/US2007/072209, 18 pages.
International Search Report, PCT/US2006/025201, 12 pages.
Communication Pursuant to Article 94(3) EPC, Application No. 05 712 091.7-1265, 4 pages.
Notification of the First Chinese Office Action, Application No. 200580003261.8, 3 pages
International Search Report and Written Opinion, PCT/US08/500346, 12 pages
PCT Invitation to Pay Additional Fees, PCT/US2007/072209, 9 pages.
"Proven reliability for quality bone marrow samples", Special Procedures, Cardinal Health, 6 pages.
F.A.S.T. 1 Intraosseous Infusion System with Depth-Control Mechanism Brochure, 6 pages.
BioAccess.com, Single Use Small Bone Power Tool - How It Works, 1 page.
International Search Report and Written Opinion, PCT/US2007/078203, 15 page.
International Search Report and Written Opinion, PCT/US2007/072202, 17 page.

International Search Report and Written Opinion, PCT/US2007/078207, 13 page.
International Search Report and Written Opinion, PCT/US2007/078205, 13 page.
Japanese Office Action, Application No. 2004-508,670, (with English summary), (13 pgs).
PCT Preliminary Report on Patentability, PCT/US/2008/050346, (8 pgs).
Japanese Office Action, Application No. 2004-508,669, (with English summary), (9 pgs).
Chinese Office Action, Application No. 200780000590.6, (with English translation), (13 pgs).
Final Office Action, U.S. Appl. No. 11/427,501, (10 pgs).
Non-Final Office Action mailed Mar. 23, 2009 and Response to Office Action filed Jun. 22, 2009, U.S. Appl. No. 11/190,331, 61 pages.
International Preliminary Report on Patentability, PCT/US/2007/078203, 13 pages.
International Preliminary Report on Patentability, PCT/US/2007/078207, 10 pages.
International Preliminary Report on Patentability, PCT/US/2007/078205, 10 pages.
International Preliminary Report on Patentability, PCT/US/2007/078204, 11 pages.
Non-Final Office Action mailed Apr. 1, 2009 and Response to Office Action filed Jul. 1, 2009, U.S. Appl. No. 10/449,503, 19 pages.
Vidacare Corporation Comments to Intraosseous Vascular Access Position Paper, Infusion Nurses Society, 6 pages.

Non-Final Office Action mailed May 13, 2009 and Response to Office Action filed Jul. 1, 2009, U.S. Appl. No. 11/427,501, 23 pages.
International Preliminary Report on Patentability, PCT/US/2007/072209, 10 pages.
Final Office Action, U.S. Appl. No. 11/781,568, 19 pages.
Final Office Action, U.S. Appl. No. 11/064,156, 12 pages.
Final Office Action, U.S. Appl. No. 11/853,685, 21 pages.
Interview Summary mailed Jul. 13, 2009 and Response to Interview Summary and Amendment filed Aug. 12, 2009, U.S. Appl. No. 11/190,331, 17 pages.
Non-Final Office Action, U.S. Appl. No. 12/259,745, 11 pages.
Non-Final Office Action, U.S. Appl. No. 11/042,912, 8 pages.
Chinese Office Action, Application No. 2005800003261, (with English translation), (9 pgs).
Request for Continued Examination and Amendment, U.S. Appl. No. 11/781,568, 9 pages.
Response to Non-Final Office Action, U.S. Appl. No. 11/042,912, (11 pgs.).
International Preliminary Report on Patentability, PCT/US2007/072202, 10 pages.
European Office Action and Search Report, Application No. 09150973.7, 8 pages.
Final Office Action, U.S. Appl. No. 11/781,597, 14 pages.
International Preliminary Report on Patentability, PCT/US08/52943, 7 pages.
Non-Final Office Action, U.S. Appl. No. 10/987,051, 9 pages.
Request for Continued Examination and Amendment, U.S. Appl. No. 11/064,156, 22 pages..

* cited by examiner

APPARATUS AND METHOD TO ACCESS BONE MARROW

RELATED APPLICATION

This application claims priority to U.S. Provisional Patent Application Ser. No. 60/384,756, filed May 31, 2002, and entitled "Apparatus and Method to Provide Access to Bone Marrow".

This application is copending to patent application entitled "Apparatus and Method to Provide Emergency Access To Bone Marrow", Ser. No. 10/449,503, filed May 30, 2003; and copending to patent application entitled "Apparatus and Method to Access the Bone Marrow for Oncology and Stem Cell Applications", Ser. No. 10/448,650, Filed May 30, 2003, which claims priority from the same provisional application.

TECHNICAL FIELD

The present invention is related in general to a medical device to access the bone marrow and specifically to an apparatus and method for penetrating the bone marrow with a powered drill and inserting a penetrator or needle.

BACKGROUND OF THE INVENTION

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

An essential element for treating all such emergencies is the rapid establishment of an intravenous (IV) line in order to administer drugs and fluids directly into the circulatory system. Whether in the ambulance by paramedics, or in the emergency room by emergency specialists, the goal is the same—to start an IV in order to administer life-saving drugs and fluids. To a large degree, the ability to successfully treat such critical emergencies is dependent on the skill and luck of the operator in accomplishing vascular access. While it is relatively easy to start an IV on some patients, doctors, nurses and paramedics often experience great difficulty establishing IV access in approximately 20 percent of patients. These patients are probed repeatedly with sharp needles in an attempt to solve this problem and may require an invasive procedure to finally establish an intravenous route.

A further complicating factor in achieving IV access occurs "in the field" e.g. at the scene of an accident or during ambulance transport where it is difficult to see the target and excessive motion make accessing the venous system very difficult.

In the case of patients with chronic disease or the elderly, the availability of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

SUMMARY OF THE INVENTION

In accordance with teachings of the present invention, an apparatus and method for gaining rapid access to the bone marrow is provided.

In one embodiment of the invention an apparatus for penetrating a bone marrow is provided that includes a housing and a penetrator assembly. The penetrator assembly is operable to penetrate the bone marrow, having a removable inner trocar and an outer penetrator. A connector operable to releasably attach the penetrator assembly to a drill shaft is included. The drill shaft is operable to connect the penetrator assembly to a gear assembly. The gear assembly is operable to engage and rotate the drill shaft. A motor operable to engage the gear assembly and drive the penetrator into the bone marrow by rotation of the drill shaft and a power supply and associated circuitry operable to power the motor are also included.

In another embodiment of the invention an apparatus for penetrating a bone marrow is provided that includes a housing and a penetrator assembly, operable to penetrate the bone marrow. A connector operable to releasably attach the penetrator assembly to a drill shaft, the drill shaft operable to connect the penetrator assembly to a reduction gear assembly is included. A reduction gear assembly operable to engage and rotate the drill shaft and a motor operable to engage the reduction gear assembly and drive the penetrator into the bone marrow by rotation of the drill shaft are also included. A power supply and associated circuitry operable to power the motor are also provided.

In one embodiment of the invention a penetrator assembly operable to provide access to a bone marrow comprising an outer penetrator and a removable inner trocar operable to penetrate the bone marrow is provided A connector operable to releasably attach the penetrator assembly to a power drill is also included.

In another embodiment of the invention a penetrator assembly operable to provide access to a bone marrow comprising an outer penetrator and a removable inner trocar operable to penetrate the bone marrow is provided. The inner trocar includes a handle, the handle including a grasping means that allows a user to grasp and manipulate the device. The outer penetrator includes a handle, the handle including a grasping means, and also includes a flange operable to engage an insertion site proximate the bone marrow. A connector operable to releasably attach the penetrator assembly to a power drill is also provided. The inner trocar is operable to releasably engage the connector.

In one embodiment of the current invention a method of accessing a bone marrow is provided that includes inserting a penetrator assembly into the bone marrow by means of a powered apparatus, detaching the powered apparatus from the penetrator, removing an inner trocar from an outer penetrator of the assembly and attaching a right angle connector to the outer penetrator.

In another embodiment of the current invention a method of accessing a bone marrow is provided that includes inserting a penetrator assembly into the bone marrow by means of a powered apparatus, detaching the powered apparatus from the penetrator, removing an inner trocar from an outer penetrator of the assembly and attaching an adapter suitable to convey medications or fluids to the bone marrow.

In yet another embodiment of the current invention a method of manufacturing an apparatus operable to penetrate a bone marrow is provided that includes manufacturing a housing having a connector operable to releasably attach a penetrator assembly to a drill shaft, a drill gear assembly, a gear assembly operable to engage and rotate the drill shaft, a motor operable to engage the gear assembly and drive a penetrator assembly into the bone marrow and a power supply and associated circuitry operable to power the motor and manufacturing a penetrator assembly operable to releasably attach to the connector.

In a further embodiment of the current invention, a kit for use in penetrating a bone marrow in an extremity is provided that includes a carrying case, an apparatus for penetrating the bone marrow including a housing and penetrator assemblies operable to penetrate the bone marrow, a removable inner trocar and an outer penetrator forming portions of at least one of the penetrator assemblies, at least one connector operable to releasably attach the penetrator assemblies to a drill shaft, a gear assembly operable to engage and rotate the drill shaft, a motor operable to engage the reduction gear assembly and drive at least one of the penetrator assemblies into the bone marrow and a power supply and associated circuitry to power the motor and a strap operable to immobilize the outer penetrator to a site in an extremity.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein.

DETAILED DESCRIPTION OF THE INVENTION

Preferred embodiments of the invention and its advantages are best understood by reference to FIGS. 1A-10 wherein like numbers refer to same and like parts.

Figure 1A:
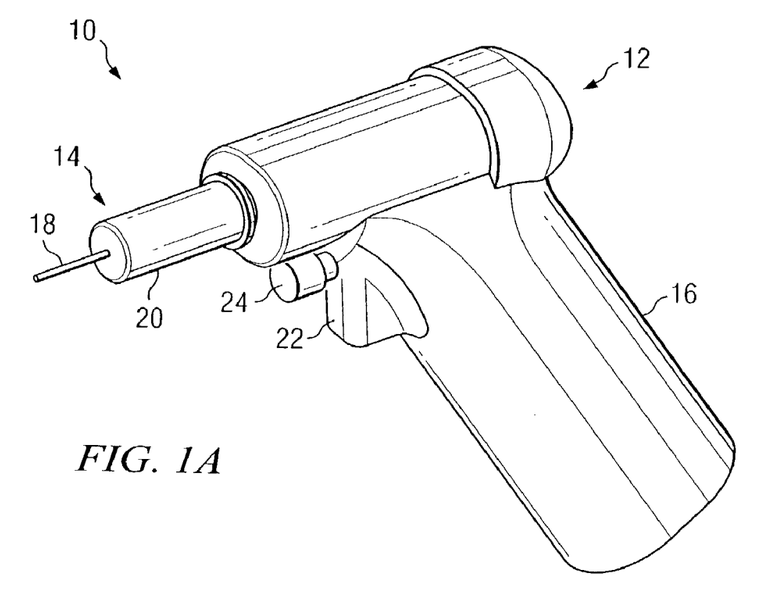
FIG. 1A is a schematic drawing showing an isometric view of one embodiment of the present invention.
Figure 1B:
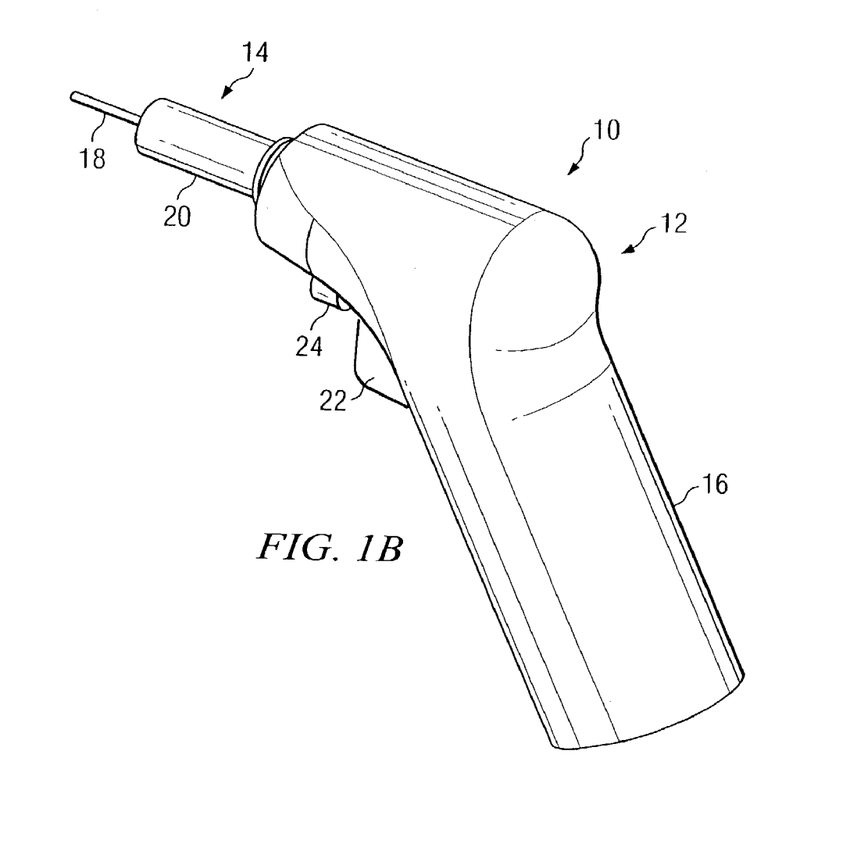
FIG. 1B is a schematic drawing showing an isometric view of one embodiment of the present invention.

Various examples of an apparatus operable to access the bone marrow in accordance with the present invention are shown generally in FIGS. 1A and 1B at 10. Apparatus 10 as shown in FIGS. 1A and 1B generally includes housing 12 and penetrator assembly 14. Housing 12 includes handle 16 that is sized and contoured to fit the hand of an operator. Handle 16 may include on/off switch 22 and safety 24. Penetrator assembly 14 includes outer penetrator 18, inner trocar (not expressly shown) and penetrator assembly connector 20.

Figure 2A:
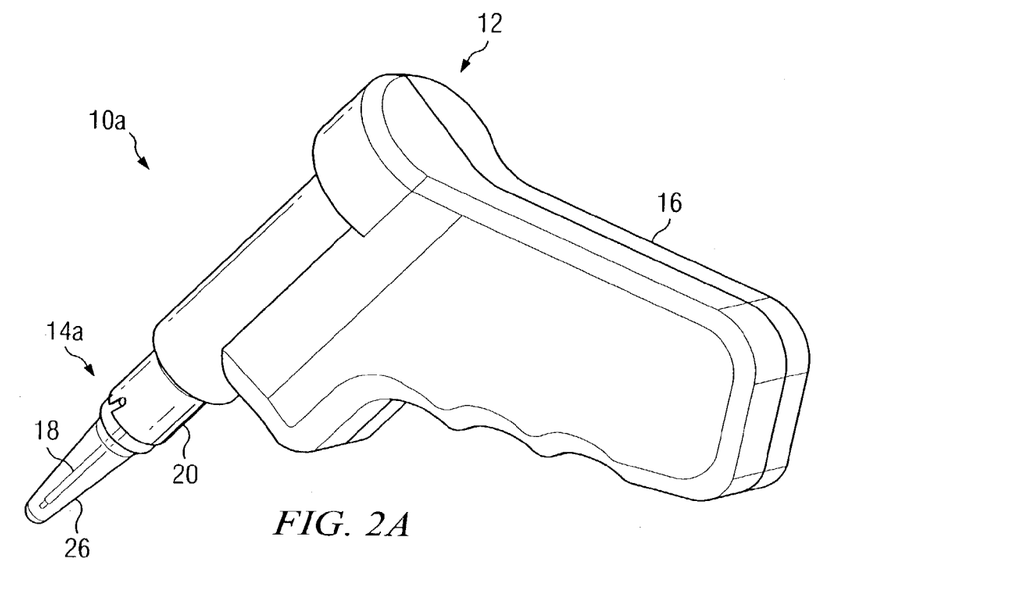
FIG. 2A is a schematic drawing showing an isometric view of one embodiment of the present invention.
Figure 2B:
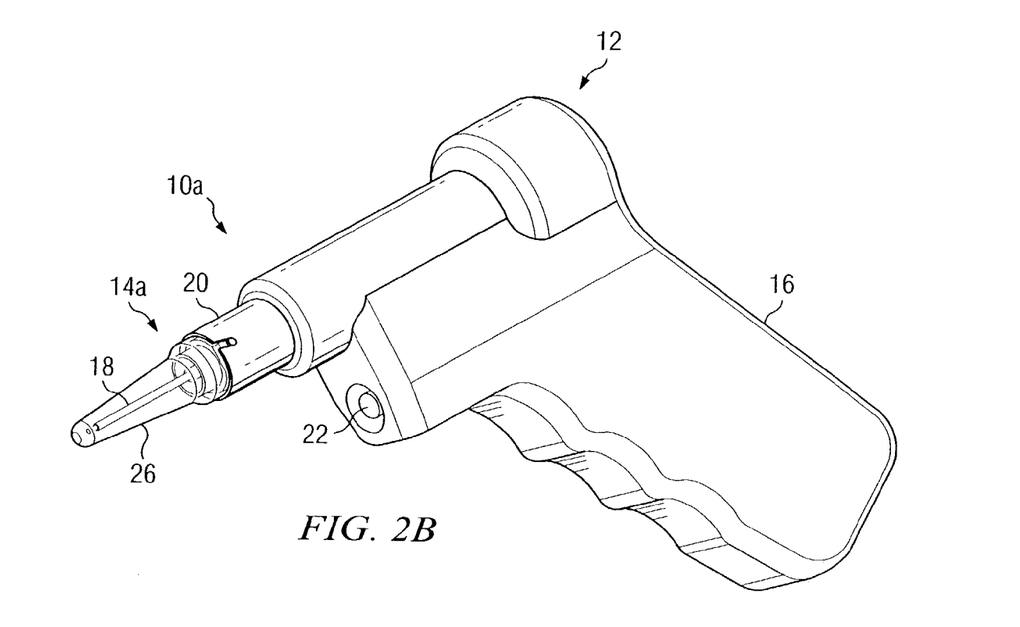
FIG. 2B is a schematic drawing showing an isometric view of one embodiment of the present invention.

FIGS. 2A and 2B illustrate an alternate embodiment of the present invention. Apparatus 10a generally includes housing 12 and penetrator assembly 14a. Housing 12 includes handle 16 that is sized and contoured to fit the hand of an operator. Handle 16 may include an on/off switch 22. Penetrator assembly 14a includes outer penetrator 18, inner trocar (not expressly shown) and penetrator assembly connector 20. Penetrator assembly 14a may include penetrator shield 26. An outer penetrator may include either a trocar, a needle, a cannula, a hollow tube, a drill bit or a hollow drill bit.

Figure 3A:
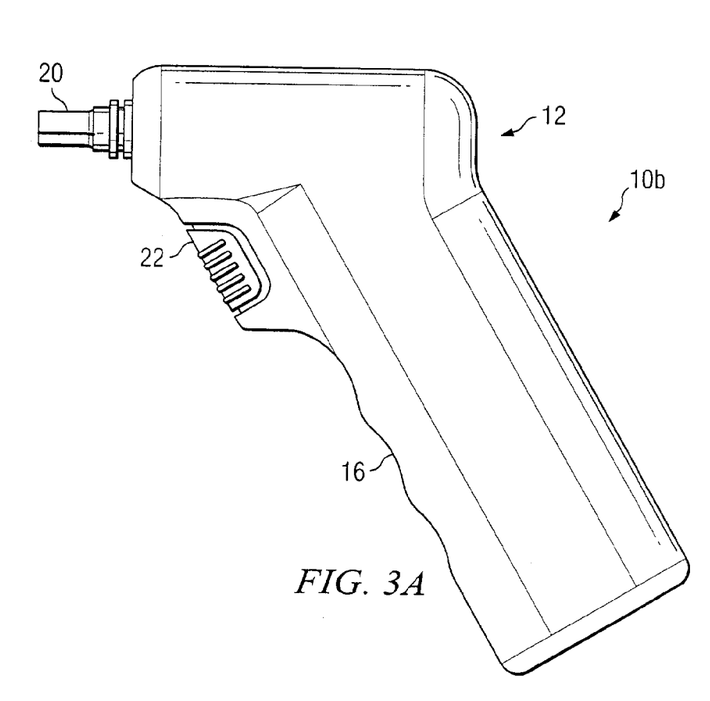
FIGS. 3A-C illustrates a side and cross-sectional view of one embodiment of the present invention.
Figure 3B:
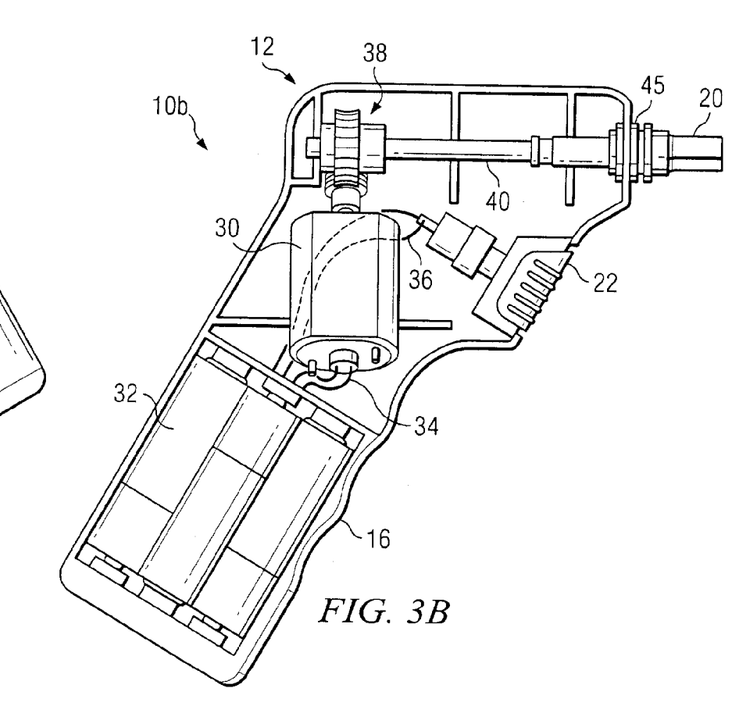
Figure 3C:
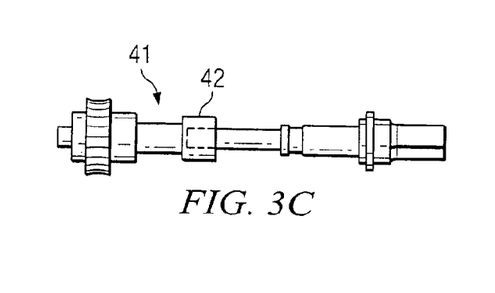

FIGS. 3A and 3B illustrate yet another embodiment of the present invention. Apparatus 10b generally includes housing 12 and a penetrator assembly (not expressly shown). Housing 12 includes handle 16 and on/off switch 22. Penetrator assembly may include penetrator (not expressly shown) and a connector, for example a pentagonal connector 20 as shown in FIG. 3A. As shown in FIG. 3B, housing 12 encloses motor 30, power supply 32, for example four or more AA batteries, motor connecting wires 34 between power supply 32 and motor 30 and switch connecting wires 36 between on/off switch 22 and power supply 32. The power supply to the apparatus may be any suitable number of AA batteries or any other type of battery, a source of direct current, a source of alternating current or a source of air or gas power. The motor may be reciprocating or rotational. Thruster bearing 45, for example a washer, may be located adjacent to housing 12 where drill shaft 40 exits housing 12. Thruster bearing 45 prevents the thrust or penetration force of drilling from being placed on gear assembly 38 as penetrator is drilled into bone. FIG. 3C shows one embodiment of the invention where drill shaft 40 may be separated into two interdigitating pieces at 42 in order to allow the two ends of drill shaft 40 to slide in and out as bone is penetrated to avoid applying excessive force to a gear assembly.

In FIG. 3B gear assembly 38 is coupled to motor 30. Gear assembly 38 may be a reduction gear assembly such as that shown in FIG. 3B that functions to reduce the revolutions per minute (RPMs) between the motor and drill shaft 40 and to increase drill shaft torque. Depending on the type of motor employed in the invention, gear assembly may or not be of the reduction type.

Figure 4A:
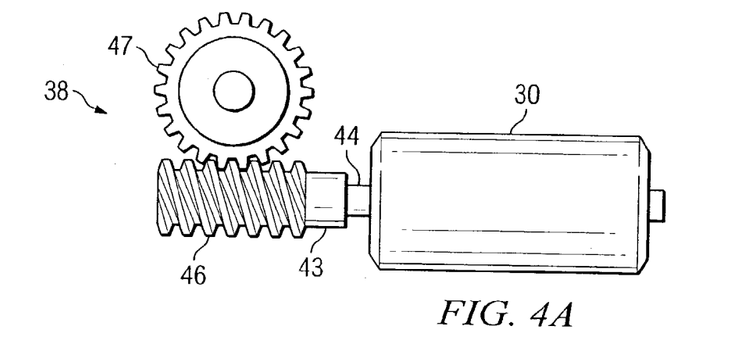
FIGS. 4A-C illustrates various alternate embodiments of a reduction gear mechanism that may be included in an embodiment of the present invention.

By way of example and not limitation, a reduction gear assembly, for example a worm gear assembly is shown in more detail in FIG. 4A and may include first connector 43 that connects shaft 44 of motor 30 to worm gear 46. Worm gear 46 may engage spur gear 47. Reduction gear assembly 38 may be used to decrease the RPMs between the motor and penetrator assembly to provide an optimum RPM at the point of insertion of penetrator assembly into bone. Reduction gear assembly 38 may also be used to increase the torque of drill shaft and drilling power.

Figure 4B:
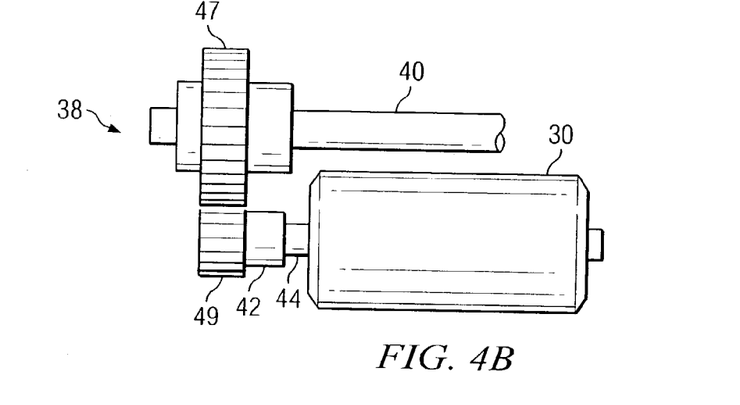
Figure 4C:
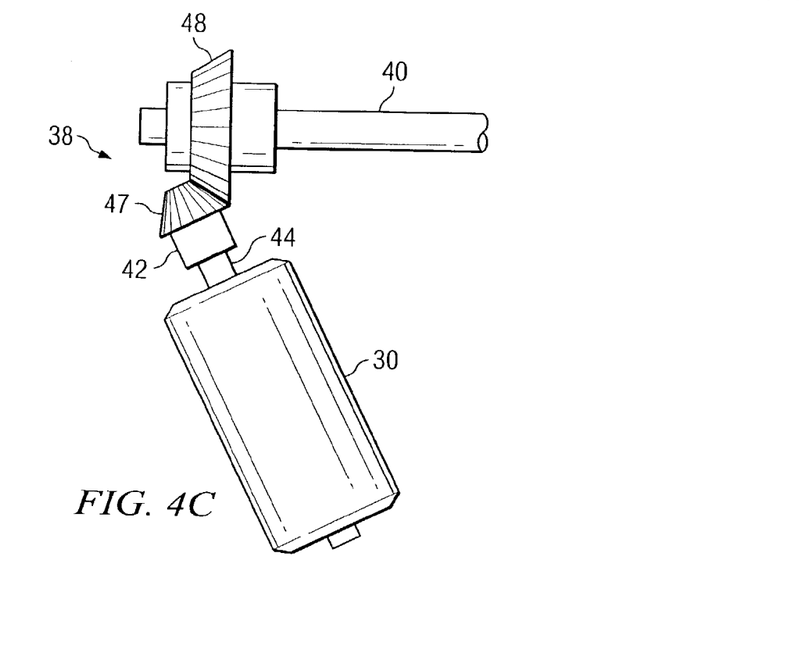

FIG. 4B illustrates one embodiment of reduction gear assembly 38 wherein a first spur gear 47 engages a second spur gear 49. FIG. 4C illustrates an alternate embodiment of reduction gear assembly 38 wherein spur gear 47 is offset from mitered gear 48 that may be preferable in some embodiments of the present invention. Other gears may be used in a reduction gear assembly, for example a planetary gear (not expressly shown) that may be used alone or in combination with a worm gear or a spur gear. In one embodiment of the current invention, gear assembly may be any suitable gear arrangement and is not limited to a reduction gear assembly.

Figure 5A:
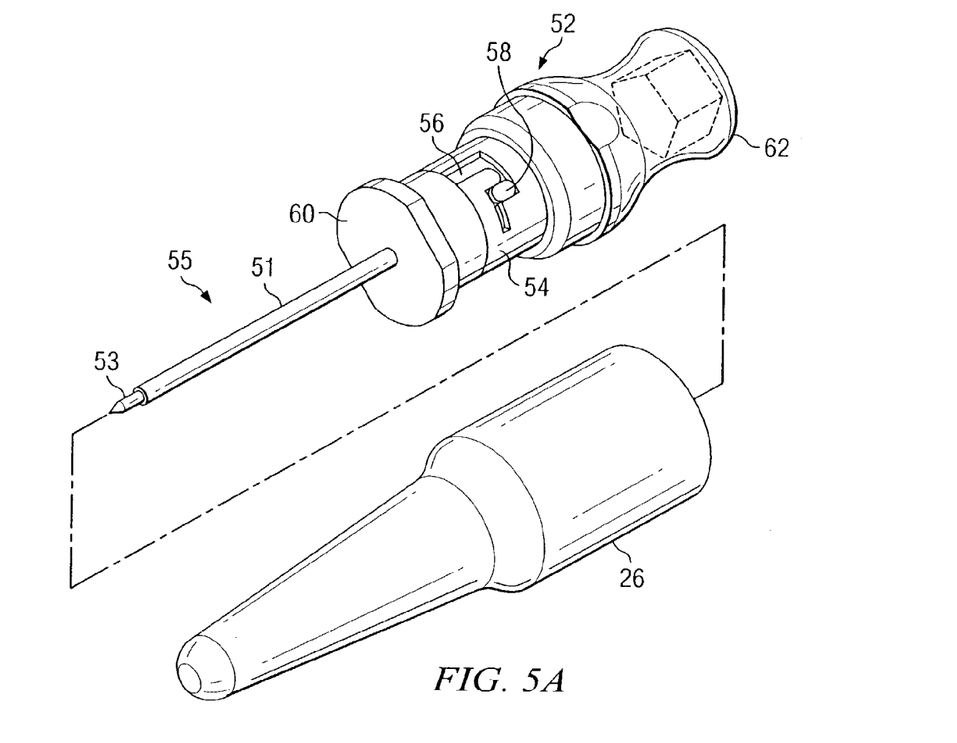
FIGS. 5A-C illustrates one embodiment of a penetrator assembly of the present invention.
Figures 5B, 5C:
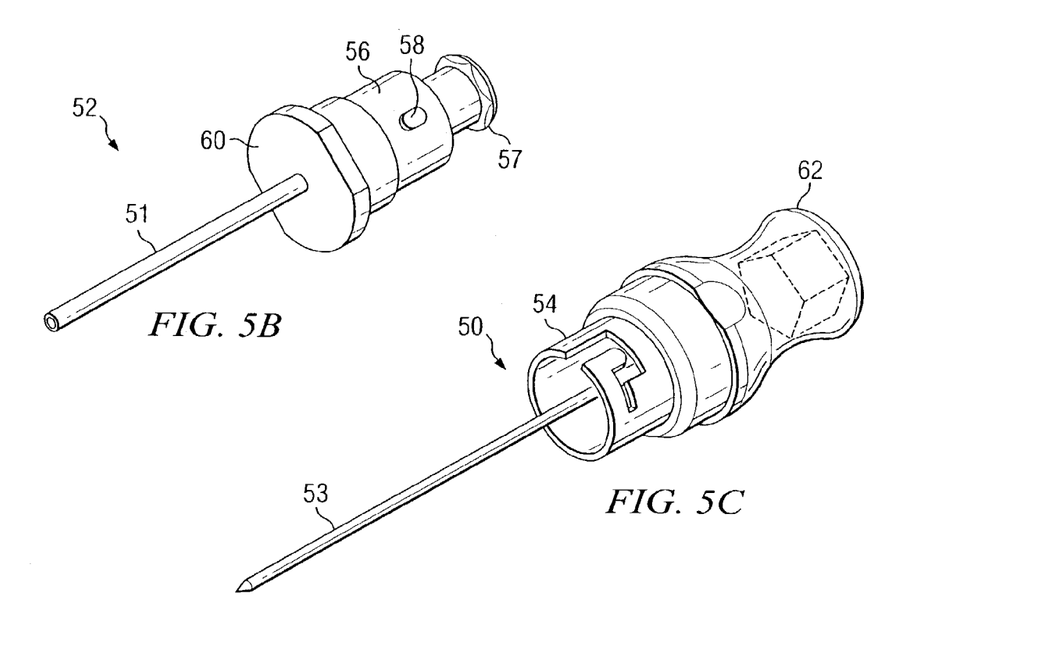

FIGS. 5A-5C illustrate one embodiment of a penetrator assembly 55 operable to penetrate a bone marrow, having a removable inner trocar 50 and an outer penetrator 52. Also shown in FIG. 5A is a penetrator shield 26 that may be used to shield penetrator assembly 55 from inadvertent engagement and also serves to preserve needle sterility. In some embodiments outer penetrator 52 may be a type of needle or cannula. FIG. 5B illustrates outer penetrator 52 may include a male connecting piece 56 operable to engage a complementary female connecting piece 54 of inner trocar 50. Adjacent to male connecting piece 56 is connecting piece locking mechanism 58 that locks into position on female connecting piece 54. Alternatively outer penetrator may include a female connecting piece suitable to engage a complementary male connecting piece of an inner trocar. Luer lock attachment 57 is coupled to male connecting piece 56 for connection to an intravenous tubing or syringe after the outer penetrator is positioned in the bone marrow. Male connecting piece 56 and female connecting piece 54 may also be of the luer-lock type. Inner trocar 50 includes stylet 53 that keeps outer penetrator 52 from getting plugged with debris created during drilling. Stylet 53 acts in combination with cannula portion 51 of outer penetrator. Outer penetrator 52 may include flange 60 that abuts or interfaces the skin of an insertion site and may be used to stabilize a penetrator assembly at the time of insertion. Penetrator assembly 55 may include various types of connectors, such as connector 62 that may be used to connect penetrator assembly 55 to a powered drill. Connector 62 may be pentagonal as shown in FIGS. 5A and 5C.

In one embodiment, the invention may include a specialized connector between the penetrator assembly and a powered drill. The connector performs at least two functions, a connecting function and a releasing function. The connecting function may be performed by various mechanisms such as a pentagonal male-female fitting or various lock-and-key mechanisms such as one that may include a combination or series of grooves and ridges or bars that match and interlock on a connector.

The releasing function may be performed by an O-ring connection, a magnetic connector, a chuck release mechanism, or a ball and detent mechanism with and without a spring. In one embodiment the releasing function may occur by means of a trigger mechanism whereby a trigger comes in contact with a holding mechanism and releases a penetrator or needle. In another embodiment a connecting mechanism may also include a trigger or retractable shield rod that slides up and contacts a holding mechanism or clamp that breaks away and releases a penetrator or needle after contact (not expressly shown).

Figure 6A:
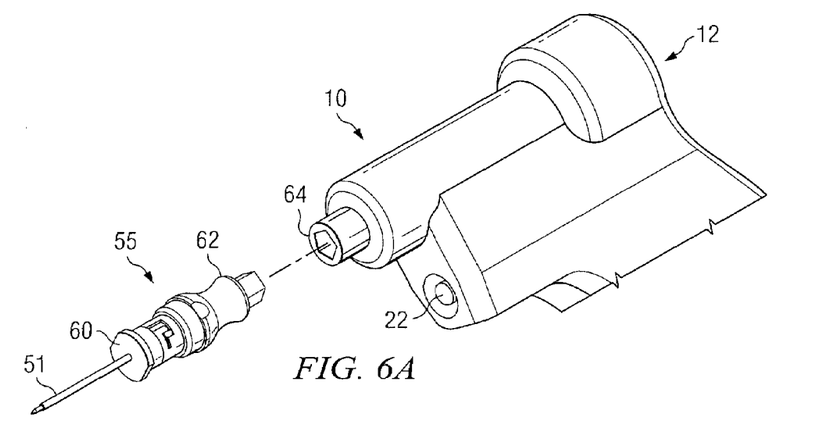
FIGS. 6A-C illustrate various alternate embodiments of a penetrator assembly connector of the present invention.

FIGS. 6A-C illustrate alternate embodiments of connectors operable to releasably attach penetrator assembly 55 to powered drill apparatus 10. FIG. 6A illustrates penetrator assembly connector 62 wherein connector 62 is formed to fit into a connector receptacle 64 and releasably lock into place. In this example, connector 62 and connector receptacle 64 are pentagonal shaped. Advantages of this embodiment may be the ease of attachment and removal of penetrator assembly 55 from powered drill apparatus 10. Penetrator assembly connector 62 may be formed from metal or plastic.

Figure 6B:
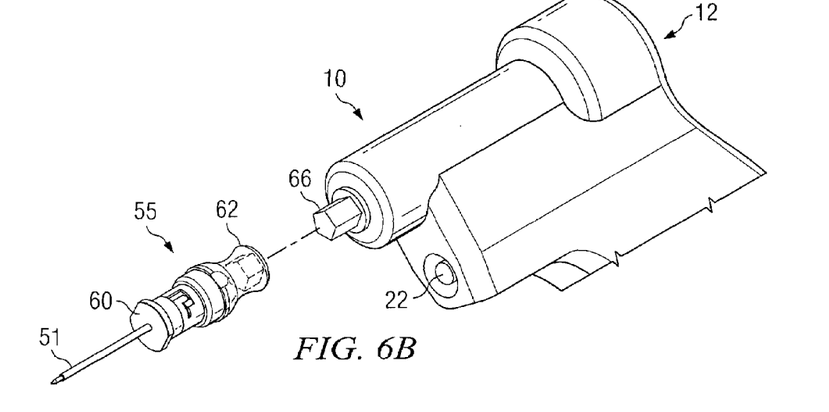
Figure 6C:
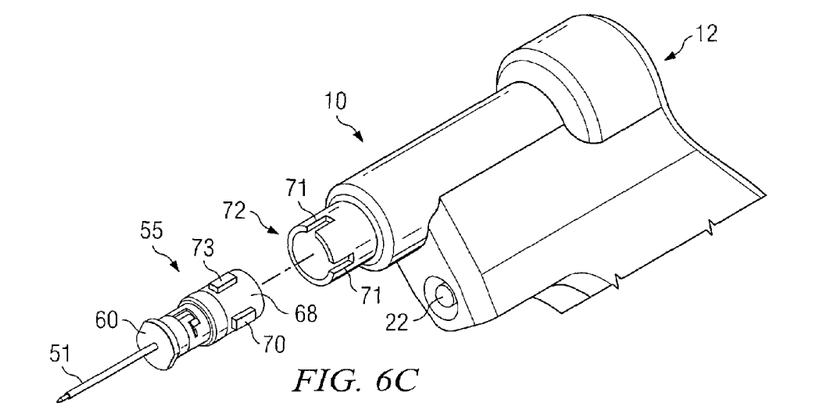

FIG. 6B illustrates an alternate embodiment of penetrator assembly connector wherein a female pentagonal receptacle 65 is operable to engage pentagonal connecting piece 66 attached to powered drill apparatus 10. FIG. 6C illustrates a further embodiment of a penetrator assembly connector wherein penetrator assembly connector 68 is a proprietary design having a pattern of ridges or bars 73 that engage a matching pattern of slots 71 on a connecting receptacle 72. Example penetrator assembly connectors may include any type of lock and key design or a pentagonal design. Penetrator assembly connectors of any type may be held in place by either a magnet, an O-ring connector or a ball and detent mechanism with or without a spring (not expressly shown).

In one embodiment, the penetrator assembly may include an outer penetrator such as a cannula, needle or hollow drill bit which may be of various sizes. Needles may be small (for pediatric patients), medium (for adults) and large (for oversized adults). Penetrator, cannulas or needles may be provided in various configurations depending on the clinical purpose for needle insertion. For example, there may be one configuration for administering drugs and fluids and an alternate configuration for sampling bone marrow or for other diagnostic purposes although one needle configuration may be suitable for both purposes. Needle configuration may vary depending on the site chosen for insertion of a needle.

Figures 7A, 7B, 7C, 7D:
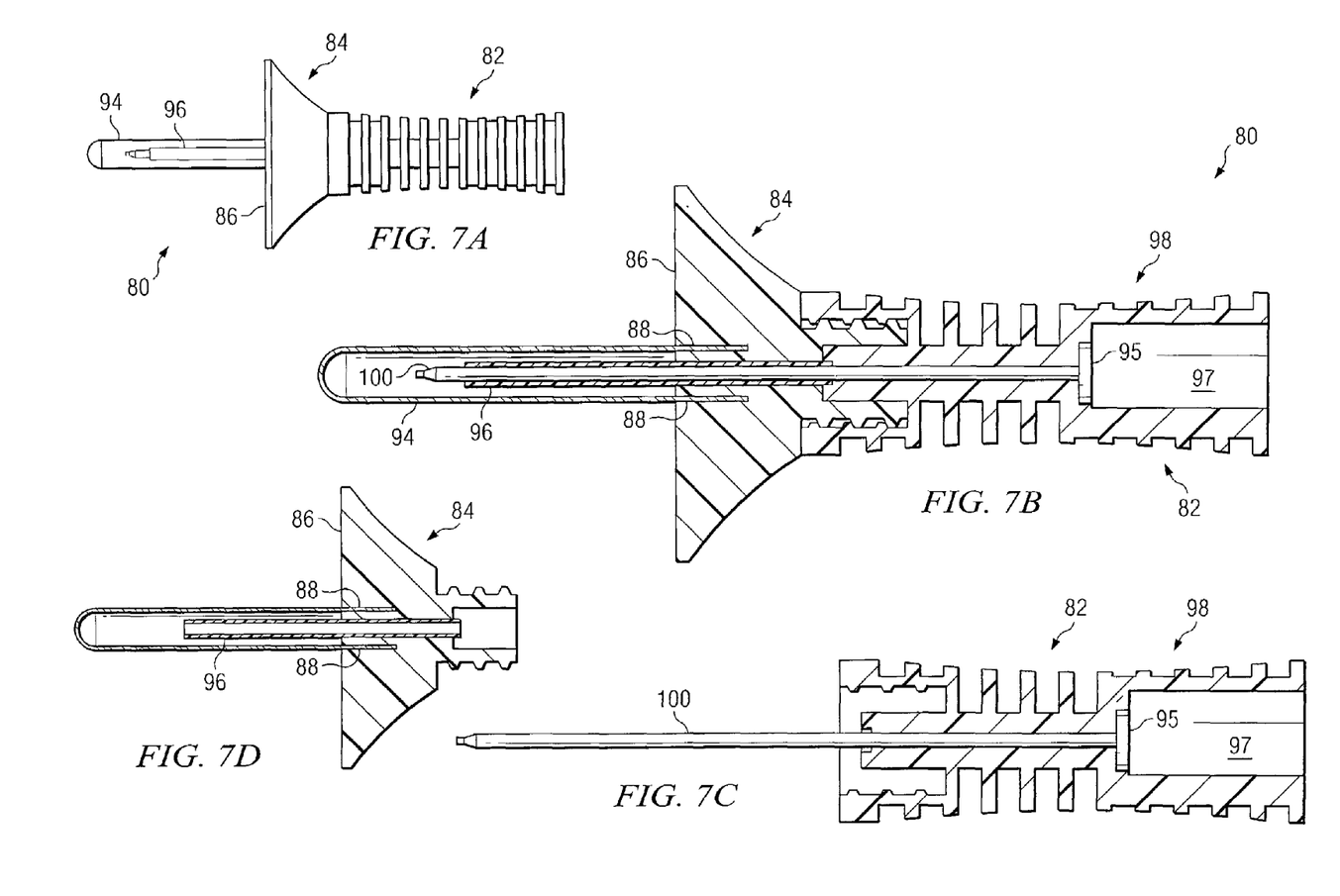
FIG. 7A illustrates one embodiment of a penetrator assembly of the present invention.
FIG. 7B illustrates a cross-sectional view of one embodiment of a penetrator assembly of the present invention.
FIG. 7C illustrates one embodiment of an inner trocar in cross section of the present invention.
FIG. 7D illustrates one embodiment of an outer penetrator in cross section of the present invention.

FIGS. 7A-7D illustrate one embodiment of a penetrator assembly 80 that includes a removable inner trocar 82 and an outer penetrator 84. FIG. 7B illustrates a cross-sectional view of one embodiment of a penetrator assembly having a removable inner trocar 82 and an outer penetrator 84. Outer penetrator 84 includes flange 86 and flange groove 88. Flange 86 may be used to stabilize penetrator assembly 80 against the skin of an insertion site. Flange groove 88 is operable to engage plastic penetrator cover 94. The surface of outer penetrator may include a series of discs formed along a longitudinal axis, a series of ridges or some other grasping means. This surface allows an operator to grasp the outer penetrator with two fingers and easily disengage the inner trocar 82 from outer penetrator 84. Outer penetrator 84 includes a penetrator cannula 96 that is hollow when stylet 100 is removed.

In FIG. 7C inner trocar 82 includes handle 98 that may have a surface such as a series of discs formed along a longitudinal axis of the trocar, or a series of ridges or some other grasping means. Handle 98 allows an operator to easily grasp and manipulate inner trocar 82 and disengage it from outer penetrator 84. Inner trocar 82 also includes stylet 100. Stylet 100 exits an end of penetrator cannula 96 when inner trocar 82 is inserted into outer penetrator 84 Stylet 100 includes a cutting tip and is operable to penetrate bone marrow. In one embodiment of the invention, inner trocar 82 may include metal disc 95 to allow a magnetic connection between penetrator assembly and powered drill. Receptacle 97 may also engage a penetrator assembly male-type connector piece operable to connect penetrating assembly to a powered drill, or any other suitable connector.

Figure 7E:
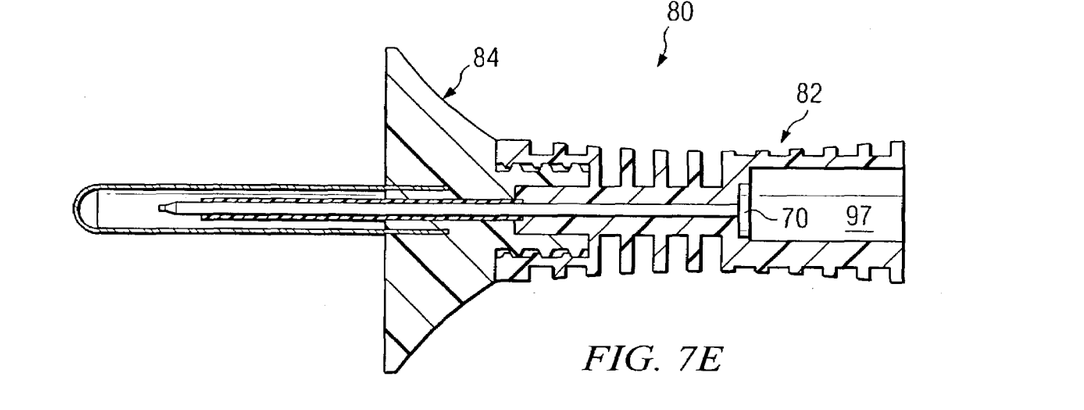
FIGS. 7E-G illustrate examples of release mechanisms of the present invention.
Figure 7F:
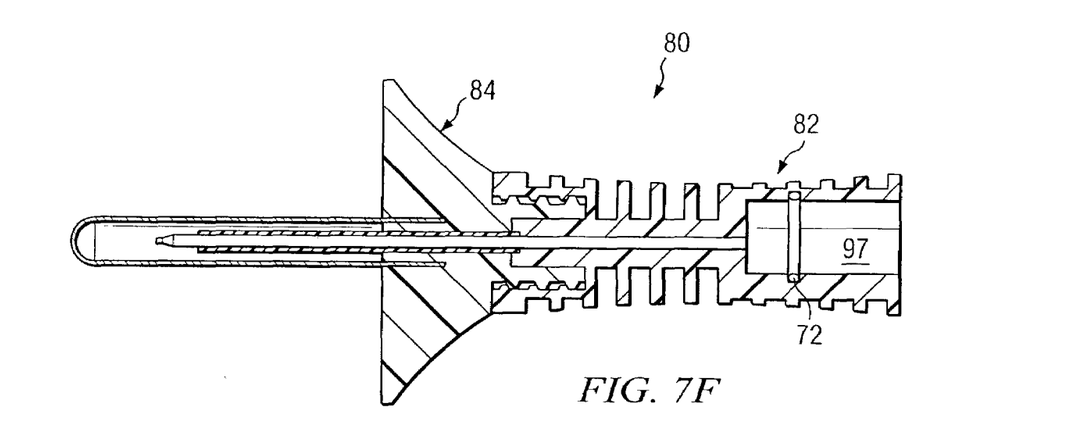
Figure 7G:
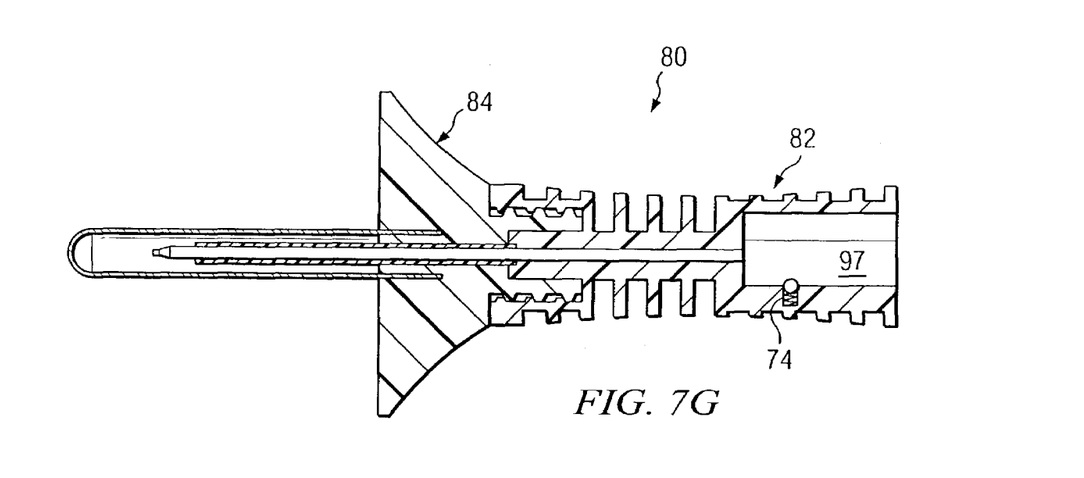

FIGS. 7E-7G illustrate example release mechanisms that may be coupled to a connector and included in penetrator assembly 80. FIG. 7E illustrates one embodiment of a magnetic release mechanism where magnetic disc 70 is included in inner trocar 82. In this embodiment magnetic disc 70 is at the base of open area or receptacle 97. In alternative embodiments a magnetic disc could be included with a pentagonal connector or a lock and key connector or any other suitable connector.

FIG. 7F illustrates another embodiment of a release mechanism where O-ring 72 is included in trocar 98 as part of a connector. In this embodiment O-ring 72 is in the wall of receptacle 97. O-ring 72 is able to engage a lock and key connector, a pentagonal connector or any other suitable connector.

FIG. 7G illustrates yet another embodiment of a release mechanism using ball and detent mechanism 74. In this embodiment ball and detent mechanism 74 is in the wall of receptacle 97. Ball and detent mechanism 74 is able to engage a lock and key connector, a pentagonal connector or any other suitable connector.

Figure 8A:
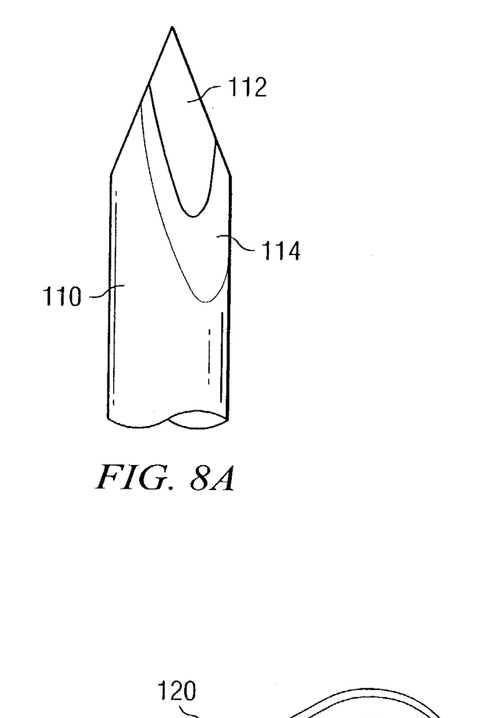
FIG. 8A illustrates one embodiment of a tip of a penetrator assembly of the present invention.

FIG. 8A illustrates an embodiment of an outer penetrator needle 110 and inner stylet 112. Cutting tip 114 of outer penetrator needle 110 and tip of inner stylet 112 are operable to penetrate bone marrow. In one embodiment of the invention the outer penetrator needle and the inner stylet are ground together as one unit in the manufacturing process to ensure that the two pieces are an exact fit and act as a single drilling unit.

Figure 8B:
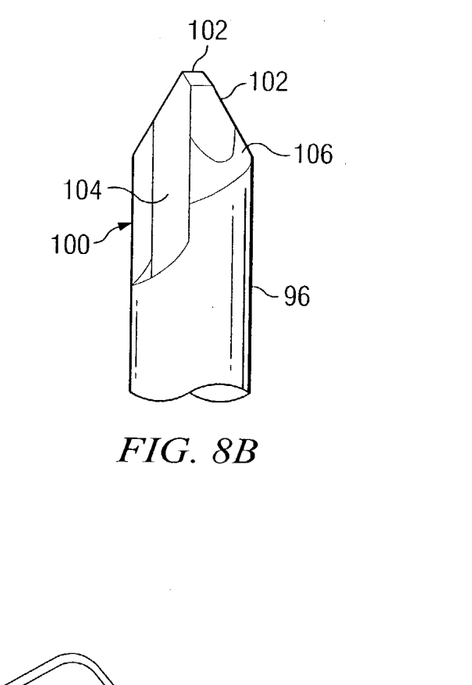
FIG. 8B illustrates one embodiment of a tip of a penetrator assembly of the present invention.

FIG. 8B illustrates another embodiment of an outer penetrator needle 96 and an inner stylet 100. Cutting tip 102 of inner stylet 100 is operable to penetrate bone marrow. Inner stylet may also include a longitudinal groove 104 that runs along the side of stylet 100 that allows bone chips and tissue to exit an insertion site as a penetrator assembly is drilled deeper into bone. Outer penetrator or needle 96 includes cutting tip 106 that facilitates insertion of outer penetrator or needle 96 and minimizes damage to outer penetrator or needle 96 as penetrator assembly 55 is inserted into bone marrow. In one embodiment of the invention the outer penetrator needle and the inner stylet are ground together as one unit in the manufacturing process to ensure that the two pieces are an exact fit and act as a single drilling unit.

Figure 9:
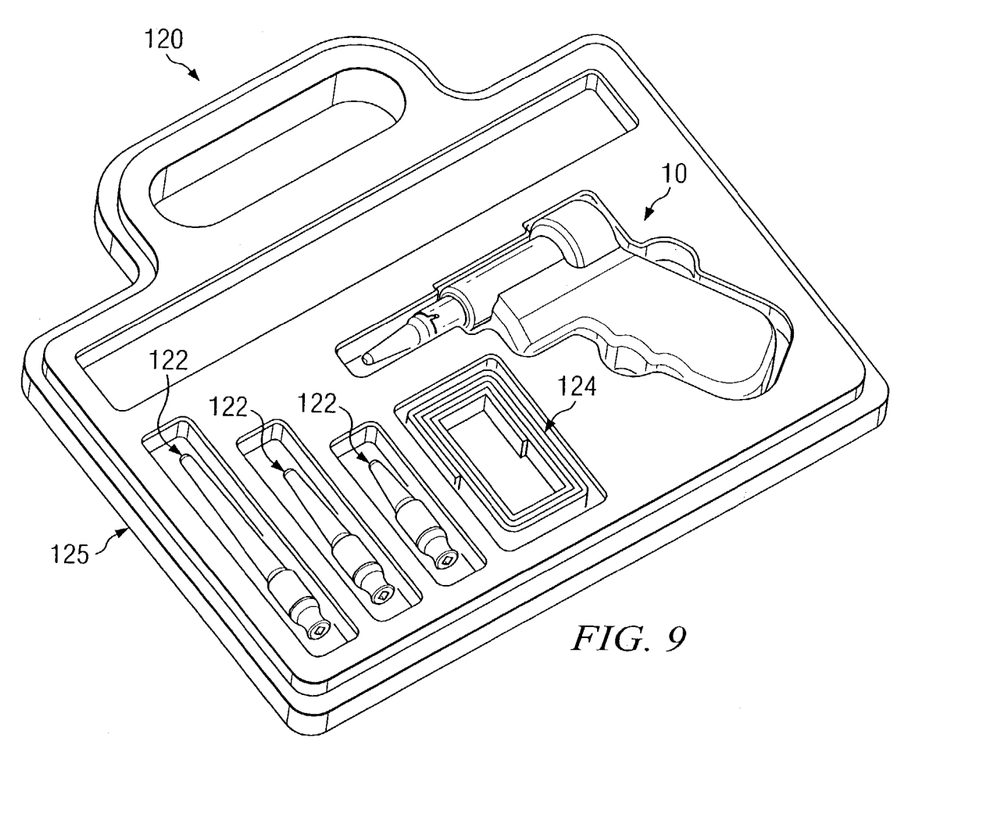
FIG. 9 illustrates one embodiment of a kit to access the bone marrow of the present invention.

FIG. 9 illustrates one embodiment of kit 120 to penetrate bone marrow. Kit 120 includes apparatus 10 for penetrating bone marrow, alternative sizes of penetrator assemblies 122, and strap 124 suitable to immobilize an outer penetrator on an extremity during insertion of penetrator assembly 122. Carrying case 125 is also included.

Figure 10:
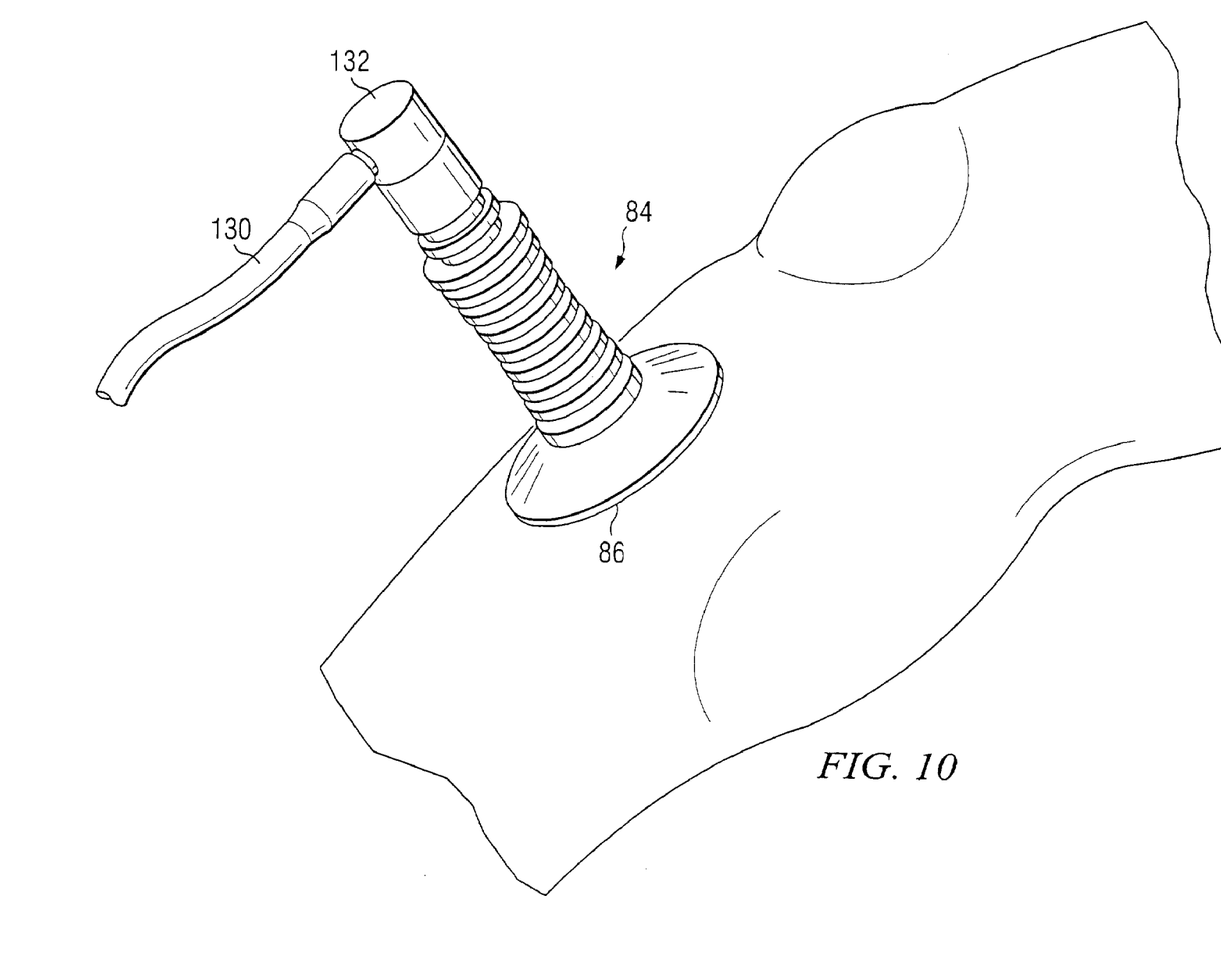
FIG. 10 illustrates one embodiment of a connector to attach to an outer penetrator of the present invention.

Once an outer penetrator or needle is inserted into a bone, it may be connected to a source of intravenous fluids or medication. FIG. 10 illustrates an example of a connector that may be used to connect the outer penetrator of a penetrator assembly to tubing 130, for example an intravenous tubing for providing intravenous fluids or medications to a person. Outer penetrator 84 is inserted into the bone marrow of an extremity. Right angle connector 132 is then used to connect intravenous tubing 130 to outer penetrator 84. Right angle connector has the advantage of allowing tubing to be connected to an outer penetrator or needle at an angle that will not kink or pinch off the lumen of the tubing. Other connectors or adapters may also be used to connect an outer penetrator to an intravenous tubing, another kind of tubing or to a syringe for use in providing medication or fluids to a person or for use in withdrawing a sample of blood from the bone marrow.

A method for providing access to the bone marrow includes using a powered drill, capable of reciprocal or rotational motion, to insert a penetrator assembly that includes an outer penetrator and an inner trocar into a bone marrow cavity. The powered drill is then released from the penetrator assembly and the inner trocar is grasped and removed from the outer penetrator. A connector present on the end of the outer penetrator, for example a luer lock connector, is then available for attachment to either an adapter, such as a right angle connector or directly to an intravenous tubing or syringe.

Although the present invention and its advantages have been described in detail, it should be understood that various changes, substitutions and alternations can be made herein without departing from the spirit and scope of the invention as defined by the following claims.

What is claimed is:

1. An apparatus for penetrating a bone marrow comprising:
    a housing defined in part by a handle sized and contoured to fit the hand of an operator;
    a penetrator assembly, comprising an inner trocar releasably engaged with an outer penetrator, operable to drill into a bone and to penetrate the associated bone marrow;
    the outer penetrator comprising a cannula;
    the inner trocar comprising a stylet wherein the stylet is operable to be inserted into the cannula of the outer penetrator;
    the outer penetrator further comprising a flange operable to stabilize the penetrator assembly against the skin at an insertion site;
    a flange groove, disposed on the flange, operable to engage a penetrator cover;
    a portion of a drill shaft extending from the housing;
    a connector receptacle and a connector operable to releasably attach the penetrator assembly to the portion of the drill shaft extending from the housing;
    a magnetic disc included with the connector, the magnetic disc operable to releasably attach the connector receptacle and the connector with each other;
    the drill shaft connected to a reduction gear assembly disposed within the housing;
    the reduction gear assembly operable to engage and rotate the drill shaft;
    a motor operable to engage the reduction gear assembly and drive the penetrator assembly into the bone marrow by rotation of the drill shaft; and
    a power supply and associated circuitry operable to power the motor.

2. The apparatus of claim 1 wherein the reduction gear assembly comprises a first shaft attached to a gear operable to engage at least one other gear.

3. The apparatus of claim 1 further comprising the reduction gear assembly offset at an angle relative to the motor.

4. The apparatus of claim 1 wherein the power supply comprises a plurality of batteries.

5. The apparatus of claim 1 wherein the power supply comprises a source of direct current.

6. The apparatus of claim 1 wherein power supply comprises at least one rechargeable battery.

7. The apparatus of claim 1 wherein the motor comprises a reciprocating motor.

8. The apparatus of claim 1 wherein the motor comprises a rotational motor.

9. The apparatus of claim 1 wherein the drill shaft comprises a first end operable to interdigitate with a second end of the drill shaft.

10. The apparatus of claim 1 wherein the drill shaft comprises a thruster bearing.

11. An apparatus for penetrating a bone marrow comprising:
    a housing defined in part by a handle sized and contoured to fit the hand of an operator;
    a drill shaft rotatably disposed in the housing with one end of the drill shaft extending from the housing;
    a penetrator assembly comprising an inner trocar releasably engaged to an outer penetrator operable to drill into a bone and associated bone marrow;
    the inner trocar comprising a stylet with a tip disposed thereon, the tip operable to penetrate bone marrow;
    the outer penetrator comprising a cannula with a cutting tip disposed thereon, the cannula operable to insert the outer penetrator into a bone and associated bone marrow;

a penetrator shield operable to preserve sterility of the stylet and the cannula;

a connector receptacle and a connector operable to releasably attach the penetrator assembly to the drill shaft;

a magnetic disc operable to releasably attach the connector receptacle and the connector with each other;

the drill shaft connected to a gear assembly disposed within the housing;

the gear assembly rotatably engaged with the drill shaft;

a motor engaged with the gear assembly whereby the penetrator assembly is driven into the bone marrow by rotation of the drill shaft when the connector receptacle and connector are releasably engaged with each other;

a power supply and associated circuitry operable to power the motor;

the connector receptacle formed as part of the penetrator assembly; and the connector formed on the one end of the drill shaft extending from the housing.

12. An apparatus for penetrating a bone marrow comprising:

a housing defined in part by a handle sized and contoured to fit the hand of an operator;

a drill shaft rotatably disposed in the housing with one end of the drill shaft extending from the housing;

a penetrator assembly comprising an outer penetrator releasably engaged with an inner trocar and operable to drill into a bone and associated bone marrow;

the penetrator assembly further comprising a metal disc;

a connector receptacle and a connector operable to releasably attach the penetrator assembly to the drill shaft;

a magnetic disc located on a receptacle on the penetrator assembly operable to releasably attach the connector receptacle and the connector with each other;

the drill shaft connected to a gear assembly disposed within the housing;

the gear assembly rotatably engaged with the drill shaft;

a motor engaged with the gear assembly whereby the penetrator assembly is driven into the bone marrow by rotation of the drill shaft when the connector receptacle and connector are releasably engaged with each other;

a power supply and associated circuitry operable to power the motor;

the connector formed as part of the penetrator assembly; and the connector receptacle formed on the one end of the drill shaft extending from the housing.

13. An apparatus for penetrating a bone marrow comprising:

a housing defined in part by a handle sized and contoured to fit the hand of an operator;

a penetrator assembly, operable to drill into a bone and to penetrate the associated bone marrow;

a connector extending from the housing;

the penetrator assembly including an inner trocar with a metal disc disposed in a connector receptacle to allow a magnetic connection between the penetrator assembly and the drill;

the connector receptacle and the magnetic disc operable to releasably attach the penetrator assembly to the connector extending from the housing;

the drill shaft connected to a reduction gear assembly disposed within the housing;

the reduction gear assembly operable to engage and rotate the drill shaft;

a motor operable to engage the reduction gear assembly and drive the penetrator assembly into the bone marrow by rotation of the drill shaft; and a power supply and associated circuitry operable to power the motor.

* * * * *